(12) United States Patent
Oskeritzian et al.

(10) Patent No.: US 12,258,586 B2
(45) Date of Patent: Mar. 25, 2025

(54) CULTURE SYSTEM AND MEDIA FOR SKIN EXPLANTS PROVIDING ENHANCED VIABILITY AND ENABLING MOLECULAR STUDIES

(71) Applicant: UNIVERSITY OF SOUTH CAROLINA, Columbia, SC (US)

(72) Inventors: Carole A. Oskeritzian, Columbia, SC (US); Alena P. Chumanevich, Lexington, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 676 days.

(21) Appl. No.: 16/658,197

(22) Filed: Oct. 21, 2019

(65) Prior Publication Data

US 2020/0131483 A1 Apr. 30, 2020

Related U.S. Application Data

(60) Provisional application No. 62/751,765, filed on Oct. 29, 2018.

(51) Int. Cl.
C12N 5/071 (2010.01)
C12N 5/00 (2006.01)
(Continued)

(52) U.S. Cl.
CPC ......... C12N 5/0698 (2013.01); C12N 5/0018 (2013.01); C12N 5/0625 (2013.01);
(Continued)

(58) Field of Classification Search
CPC .. C12N 5/0698; C12N 5/0018; C12N 5/0625; C12N 2501/125; C12N 2501/998; C12N 5/0629; C12Q 1/6809; G01N 33/6803
See application file for complete search history.

(56) References Cited

U.S. PATENT DOCUMENTS

| | | | | |
|---|---|---|---|---|
| 2014/0140967 A1* | 5/2014 | Saeki | ........................ | A61P 3/06 |
| | | | | 435/375 |
| 2015/0126923 A1* | 5/2015 | Falo, Jr. | ................ | A61K 9/0021 |
| | | | | 264/255 |
| 2017/0065554 A1* | 3/2017 | Heiman | ..................... | A61P 3/10 |

OTHER PUBLICATIONS

Mazzalupo et al., The Journal of Investigative Dermatology, vol. 118, No. 5, May 2002, pp. 866-870 (Year: 2002).*

(Continued)

*Primary Examiner* — Jeremy C Flinders
*Assistant Examiner* — Thomas R. Amick
(74) *Attorney, Agent, or Firm* — DORITY & MANNING, P.A.

(57) ABSTRACT

Embodiments of the invention include systems and media for mammalian cell culture that enhance cell viability which enables biological assays and quantitative studies in tissues such as skin explants. Certain embodiments may be used in coordination with each other or may be practiced separately. An exemplary embodiment of the invention is a culture medium that includes Dulbecco's Modified Eagle's Medium, X-VIVO medium, and subcutaneous adipocyte medium. In one embodiment the culture medium includes approximately 30-60% Dulbecco's Modified Eagle's Medium by volume, approximately 30-60% X-VIVO medium by volume, and approximately 2.5-15% subcutaneous adipocyte medium by volume. Certain embodiments of the culture medium can also include recombinant human stem cell factor. Embodiments of the invention disclosed here are not limited to the brands described and encompass equivalents, as well as combinations, of the individual chemical components that make up the media described herein.

15 Claims, 7 Drawing Sheets

Specification includes a Sequence Listing.

(51) Int. Cl.
C12Q 1/6809 (2018.01)
G01N 33/68 (2006.01)
(52) U.S. Cl.
CPC ....... *C12Q 1/6809* (2013.01); *G01N 33/6803* (2013.01); *C12N 2501/125* (2013.01)

(56) References Cited

OTHER PUBLICATIONS

Cosar et al., Nature Communications, 7:10686, 2016, pp. 1-13 (Year: 2016).*
Medvec et al., Molecular Therapy: Methods & Clinical Development vol. 8, Mar. 2018, pp. 65-74 (Year: 2018).*
Minteer et al., Dissertation, University of Pittsburgh, Swanson School of Engineering, Mar. 2, 2015 (Year: 2015).*
Salvagiotto et al., PLoS One Mar. 2011 6(3): e17829, pp. 1-9 (Year: 2011).*
Zen-Bio Instruction Manual, Subcutaneous Human Adipocytes, 2008, 14 pages, retrieved from the internet: https://www.zen-bio.com/pdf/ZBM000100SQAdipocyteCareRV0508.pdf (Year: 2008).*
ZenBio, Advanced Cell-Based Solutions & Services, Product Information, 7 pages, retrieved from the internet May 19, 2022: https://www.zen-bio.com/products/media/subcutaneous_adipocytes.php (Year: 2022).*
Cho et al., Med Lasers 2013;2(2): 58-63 (Year: 2013).*
Costa et al., J. Exp. Med, vol. 183, Jun. 1996, pp. 2681-2686 (Year: 1996).*
Frade et al., An Bras Dermatol. 2015; 90(3):347-50 (Year: 2015).*
Grabbe et al., Arch Dermatol Res (1994) 287: 78-84 (Year: 1994).*
Majewska-Szczepanik et al., J Allergy Clin Immunol, Jul. 2016, vol. 138, No. 1, pp. 262-273 and 273.e1-273.e6 (Year: 2016).*
Schmidt et al Development 140, 1517-1527 (2013) (Year: 2013).*
Lu, Z., Hasse, S., Bodo, E., Rose, C., Funk, W. and Paus, R. , Towards the development of a simplified long-term organ culture method for human scalp skin and its appendages under serum-free conditions. Experimental Dermatology, 16: 37-44. (Year: 2006).*
Adamson-Small L et al. Sodium Chloride Enhances Recombinant Adeno-Associated Virus Production in a Serum-Free Suspension Manufacturing Platform Using the Herpes Simplex Virus System. Hum Gene Ther Methods. Feb. 2017;28(1):1-14 (Year: 2017).*
Millipore product information DMEM (Year: 2015).*
Tausk. (Tausk, F., and B. Undem. "Exogenous but not endogenous substance P releases histamine from isolated human skin fragments." Neuropeptides 29.6 (1995): 351-355.). (Year: 1995).*
Akin, et al. "Mast cell activation syndrome: Proposed diagnostic criteria" *J. Aller. Clin. Immun.* 126 (2010) pp. 1099-1104.
Allende, et al. "Mice deficient in sphingosine kinase 1 are rendered lymphopenic by FTY720" *J. Biol. Chem.* 279 (2004) pp. 52487-52492.
Anderson, et al. "A fractal analysis of the radial distribution of bronchial capillaries around large airways" *J. Appl. Physiol.* 98 (2005) pp. 850-855.
Ando, et al. "Mast cells are required for full expression of allergen/SEB-induced skin inflammation" *J. Invest. Dermatol.* 133 (2013) pp. 2695-2705.
Aon, et al. "The scale-free dynamics of eukaryotic cells" *PLoS One* 3:e3624 (2008) pp. 1-12.
Arock, et al. "Differentiation of human basophils: An overview of recent advances and pending questions" *J. Leuk. Biol.* 71 (2002) pp. 557-564.
Auriemma, et al. "Cytokines and T cells in atopic dermatitis" *Euro. Cytok. Net.* 24 (2013) pp. 37-44.
Bandhuvula, et al. "The immune modulator FTY720 inhibits sphingosine-1-phosphate lyase activity" *J. Biol. Chem.* 280 (2005) pp. 33697-33700.
Bojanowski, K. "Hypodermal delivery of cosmetic actives for improved facial skin morphology and functionality" *Int'l J. Cosm. Sci.* 35 (2013) pp. 562-567.

Brown, et al. "The fractal nature of nature: Power laws, ecological complexity and biodiversity" *Phil. Trans. Roy. Soc. London B* 357 (2002) pp. 619-626.
Chumanevich, et al. "Sphingosine-1-phosphate/sphingosine-1-phosphate receptor 2 axis can promote mouse and human primary mast cell angiogenic potential through upregulation of vascular endothelial growth factor-A and matrix metalloproteinase-2" *Med. Inflamm.* 2016:1503206 (2016) pp. 1-8.
Crompton, et al. "Oestrogen promotes healing in a bacterial LPS model of delayed cutaneous wound repair" *Lab. Invest.* 96 (2016) pp. 439-449.
Da Silva, et al. "Mast cell function: A new vision of an old cell" *J. Histochem. Cytochem.* 62 (2014) pp. 698-738.
Damsgaard, et al. "Mast cells and atopic dermatitis. Stereological quantification of mast cells in atopic dermatitis and normal human skin" *Arch. Derma. Res.* 289 (1997) pp. 256-260.
Darlenski, et al. "Atopic dermatitis as a systemic disease" *Clin Derma.* 32 (2014) pp. 409-413.
Di Leva, A. (2012). "Fractal analysis of microvascular networks in malignant brain tumors" *Clin. Neuropath.* 31 (2012) pp. 342-351.
Di Leva, et al. "Fractal dimension as a quantitator of the microvasculature of normal and adenomatous pituitary tissue" *J. Anat.* 211 (2007) pp. 673-680.
Dillahunt, et al. "Usage of sphingosine kinase isoforms in mast cells is species and/or cell type determined" *J. Immun.* 190 (2013) pp. 2058-2067.
Dioguardi, et al. "Metrically measuring liver biopsy: a chronic hepatitis B and C computer-aided morphologic description" *World J. Gastro.* 14 (2008) pp. 7335-7344.
Dioguardi, et al. "Liver fibrosis and tissue architectural change measurement using fractal-rectified metrics and Hurst's exponent" *World J. Gastro.* 12 (2006) pp. 2187-2194.
Dong, et al. "Different doses of lipopolysaccharides regulate the lung inflammation of asthmatic mice via TLR4 pathway in alveolar macrophages" *J. Asthma* 46 (2009) pp. 229-233. (Abstract only).
Doubal, et al. "Fractal analysis of retinal vessels suggests that a distinct vasculopathy causes lacunar stroke" *Neurology* 74 (2010) pp. 1102-1107.
Eisenbarth, et al. "Lipopolysaccharide-enhanced, toll-like receptor 4-dependent T helper cell type 2 responses to inhaled antigen" *J. Exp. Med.* 196 (2002) pp. 1645-1651.
Elias, P.M. "Lipid abnormalities and lipid-based repair strategies in atopic dermatitis" *Biochim. Biophys. Acta.* 1841 (2014) pp. 323-330.
Ewald, et al. "Meta-analysis derived atopic dermatitis (MADAD) transcriptome defines a robust AD signature highlighting the involvement of atherosclerosis and lipid metabolism pathways" *BMC Med. Genomics* 8:60 (2015) pp. 1-15.
Eyerich, et al. "Immunology of atopic eczema: overcoming the Th1/Th2 paradigm" *Allergy* 68 (2013) pp. 974-982.
Ferro, et al. "Fractal characteristics of May-Grünwald-Giemsa stained chromatin are independent prognostic factors for survival in multiple myeloma" *PLoS One* 6:e20706 (2011) pp. 1-8.
Fuseler, et al. "Modulation of the migration and differentiation potential of adult bone marrow stromal stem cells by nitric oxide" *Biomaterials* 33 (2012) pp. 1032-1043.
Fuseler, et al. "Fractal and image analysis of the microvasculature in normal intestinal submucosa and intestinal polyps in $Apc^{Min/+}$ mice" *Micro. Microanal.* 16 (2010) pp. 73-79.
Fuseler, et al. "Fractal and image analysis of morphological changes in the actin cytoskeleton of neonatal cardiac fibroblasts in response to mechanical stretch" *Micro. Microanal.* 13 (2007) pp. 133-143.
Fuseler, et al. "Analysis and quantitation of NF-κB nuclear translocation in tumor necrosis factor alpha (TNF-α) activated vascular endothelial cells" *Micro. Microanal.* 12 (2006) pp. 269-276.
Galli, et al. "IgE and mast cells in allergic disease" *Nat. Med.* 18 (2012) pp. 693-704.
Galli, et al. Phenotypic and functional plasticity of cells of innate immunity: Macrophages, mast cells and neutrophils. *Nat. Immun.* 12 (2011) pp. 1035-1044.
Galli, et al. "Immunomodulatory mast cells: Negative, as well as positive, regulators of immunity" *Nat. Rev. Immun.* 8 (2008) pp. 478-486.

(56) References Cited

OTHER PUBLICATIONS

Gerber, et al. "The top skin-associated genes: A comparative analysis of human and mouse skin transcriptomes" *Biol. Chem.* 395 (2014) pp. 577-591. (Abstract only).
Giannou, et al. "Mast cells mediate malignant pleural effusion formation" *J. Clin. Invest.* 125 (2015) pp. 2317-2334.
Gittler, et al. "Progressive activation of $T_H2/T_H22$ cytokines and selective epidermal proteins characterizes acute and chronic atopic dermatitis" *J. Allergy Clin. Immun.* 130 (2012) pp. 1344-1354.
Gonzalo, et al. "Coordinated involvement of mast cells and T cells in allergic mucosal inflammation: critical role of the CC chemokine ligand 1:CCR8 axis" *J. Immun.* 179 (2007) pp. 1740-1750.
Graham, et al. "Lessons learned from mice and man: mimicking human allergy through mouse models" *Clin. Immun.* 155 (2014) pp. 1-16.
Griffith, et al. "Chemokines and chemokine receptors: positioning cells for host defense and immunity" *Ann. Rev. Immun.* 32 (2014) pp. 659-702.
Grimbaldeston, et al. "Mast cell-deficient *W-sash c-kit* mutant $Kit^{W-sh/W-sh}$ mice as a model for investigating mast cell biology in vivo" *Am. J. Pathol.* 167 (2005) pp. 835-848.
Grizzi, et al. "Quantitative evaluation and modelling of two-dimensional neovascular network complexity: The surface fractal dimension" *BMC Cancer* 5 (2005) pp. 14-23.
Grizzi, et al. "A fractal scoring system for quantifying active collagen synthesis during chronic liver disease" *Int. J. Chaos Theory Appl.* 21 (1999) pp. 262-266.
Haas, et al. "Demonstration of the high-affinity IgE receptor (FcεRI) on Langerhans cells of oral mucosa" *Exp. Dermatol.* 2 (1993) pp. 157-160.
Hait, et al. "Regulation of histone acetylation in the nucleus by sphingosine-1-phosphate" *Science* 325 (2009) pp. 1254-1257.
Hamilton, et al. "Mast cell activation syndrome: A newly recognized disorder with systemic clinical manifestations" *J. Allergy Clin. Immun.* 128 (2011) pp. 147-152.
Hart, et al. "Age-related changes in dermal mast cell prevalence in BALB/c mice: Functional importance and correlation with dermal mast cell expression of Kit" *Immunology* 98 (1999) pp. 352-356.
Hart, et al. "Dermal mast cells determine susceptibility to ultraviolet B-induced systemic suppression of contact hypersensitivity responses in mice" *J. Exp. Med.* 187 (1998) pp. 2045-2053.
He, et al. "Epicutaneous antigen exposure induces a Th17 response that drives airway inflammation after inhalation challenge" *PNAS* 104 (2007) pp. 15817-15822.
Ishikawa, et al. "Local skin response in mice induced by a single intradermal injection of bacterial lipopolysaccharide and lipid A" *Infect. Immun.* 59 (1991) pp. 1954-1960.
Japtok, et al. "Sphingosine-1-phosphate as signaling molecule in the skin: relevance in atopic dermatitis" *Allergo J. Int.* 23 (2014) pp. 54-59.
Japtok, et al. "Sphingosine 1-phosphate modulates antigen capture by murine Langerhans cells via the $S1P_2$ receptor subtype" *PLoS One* 7:e49427 (2012).
Jelinek, et al. "The morphology and classification of a ganglion cells in the rat retinae: A fractal analysis study" *J. Neurosci. Meth.* 201 (2011) pp. 281-287.
Kalesnikoff, et al. "New developments in mast cell biology" *Nat. Immun.* 9 (2008) pp. 1215-1223.
Kambe, et al. "Human skin-derived mast cells can proliferate while retaining their characteristic functional and protease phenotypes" *Blood* 97 (2001) pp. 2045-2052.
Kawakami, et al. "Mast cells in atopic dermatitis" *Curr. Opin. Immun.* 21 (2009) pp. 666-678.
Kendall, et al. "Bioactive lipid mediators in skin inflammation and immunity" *Prog. Lipid Res.* 52 (2013) pp. 141-164.
Kim, et al. "Time-dependent progression from the acute to chronic phases in atopic dermatitis induced by epicutaneous allergen stimulation in NC/Nga mice" *Exp. Derma.* 23 (2014) pp. 53-57.
Lagunoff, D. "Analysis of dye binding sites in mast cell granules" *Biochemistry* 19 (1974) pp. 3982-3986.
Le Stunff, et al. "Recycling of sphingosine is regulated by the concerted actions of sphingosine-1-phosphate phosphohydrolase 1 and sphingosine kinase 2" *J. Biol. Chem.* 282 (1997) pp. 34372-34380.
Leung, et al. "Deciphering the complexities of atopic dermatitis: shifting paradigms in treatment approaches" *J. Allergy Clin. Immun.* 134 (2014) pp. 769-779.
Liu, et al. "IgE, mast cells, and eosinophils in atopic dermatitis" *Clin. Rev. Allergy Immun.* 41 (2011) pp. 298-310.
Macritchie, et al. "Effect of the sphingosine kinase 1 selective inhibitor, PF-543 on arterial and cardiac remodelling in a hypoxic model of pulmonary arterial hypertension" *Cell Signal* 28 (2016) pp. 946-955.
Malajian, et al. "New pathogenic and therapeutic paradigms in atopic dermatitis" *Cytokine* 73 (2015) pp. 311-318.
Mandelbrot, B.B. "The Fractal Geometry of Nature" *W.H. Freeman and Co.* $1^{st}$ Ed. (1982) pp. 1-461.
Manera, et al. "The use of fractal dimension and lacunarity in the characterization of mast cell degranulation in rainbow trout (*Onchorhynchus mykiss*)" *J. Micro.* 256 (2014) pp. 82-89.
Marshall, J.S. "Mast-cell responses to pathogens" *Nat. Rev. Immun.* 4 (2004) pp. 787-799.
McAlpine, et al. "Virus stimulation of human mast cells results in the recruitment of $CD56^+T$ cells by a mechanism dependent on CCR5 ligands" *FASEB J.* 26 (2012) pp. 1280-1289.
McNally, et al. "Fractal geometry in the nucleus" *EMBO J.* 29 (2010) pp. 2-3.
Metzger, et al. "The receptor with high affinity for immunoglobulin E" *Ann. Rev. Immun.* 4 (1986) pp. 419-470.
Mitra, et al. "Role of ABCC1 in export of sphingosine-1-phosphate from mast cells" *PNAS* 103 (2006) pp. 16394-16399.
Moledina, et al. "Fractal branching quantifies vascular changes and predicts survival in pulmonary hypertension: a proof of principle study" *Heart* 97 (2011) pp. 1245-1249.
Moon, et al. "Mast cell mediators: Their differential release and the secretory pathways involved" *Front. Immun.* 5 (2014) pp. 1-18.
Mu, et al. "Molecular biology of atopic dermatitis" *Clin. Rev. Allergy Immun.* 47 (2014) pp. 193-218.
Nakamura, et al. "*Staphylococcus* δ-toxin induces allergic skin disease by activating mast cells" *Nature* 503 (2013) pp. 397-401.
Nakatsuji, et al. "Antimicrobials from human skin commensal bacteria protect against *Staphylococcus aureus* and are deficient in atopic dermatitis" *Sci. Trans. Med.* 9 (2017) pp. 1-11.
Nezadal, et al. "The Boxcounting: Critical Study" *Proc. 4th Conf. Pred. Synerg. More* (2001).
Nussbaum, et al. "Sphingosine-1-phosphate receptor 3 promotes leukocyte rolling by mobilizing endothelial Pselectin" *Nat. Comm.* 6:6416 (2015) pp. 1-12.
Ohsawa, et al. "The antagonism of histamine H1 and H4 receptors ameliorates chronic allergic dermatitis via anti-pruritic and anti-inflammatory effects in NC/Nga mice" *Allergy* 67 (2012) pp. 1014-1022.
Oizumi, et al. "Pseudomonas-derived ceramidase induces production of inflammatory mediators from human keratinocytes via sphingosine-1-phosphate" *PLoS One* 9:e89402 (2014).
Oldford, et al. "Mast cells as targets for immunotherapy of solid tumors" *Mol. Immun.* 63 (2015) pp. 113-124.
Oskeritzian, et al. "The sphingosine-1-phosphate/sphingosine-1-phosphate receptor 2 axis regulates early airway T-cell infiltration in murine mast cell-dependent acute allergic responses" *J. Aller. Clin. Immun.* 135 (2015) pp. 1008-1018.
Oskeritzian, C.A. "Mast cell plasticity and sphingosine-1-phosphate in immunity, inflammation and cancer" *Mol. Immun.* 63 (2015) pp. 104-112.
Oskeritzian, et al. "Essential roles of sphingosine-1-phosphate receptor 2 in human mast cell activation, anaphylaxis, and pulmonary edema" *J. Exper. Med.* 207 (2010) pp. 465-474.
Oskeritzian, et al. "Distinct roles of sphingosine kinases 1 and 2 in human mast-cell functions" *Blood* 111 (2008) pp. 4193-4200.
Patrizi, et al. "Atopic dermatitis and the atopic march: what is new?" *J. Allergy* 2011:279425 (2011) pp. 1-5.

(56) References Cited

OTHER PUBLICATIONS

Price, et al. "A specific sphingosine kinase 1 inhibitor attenuates airway hyperresponsiveness and inflammation in a mast cell-dependent murine model of allergic asthma" *J. Aller. Clin. Immun.* 131 (2013) pp. 501-511.
Qian, et al. "Fractal dimension as a measure of altered actin cytoskeleton in MC3T3-E1 cells under simulated microgravity using 3-D/2-D clinostats" *IEEE Trans. Biomed. Eng.* 59 (2012) pp. 1374-1380.
Rafail, et al. "Complement deficiency promotes cutaneous wound healing in mice" *J. Immun.* 194 (2015) 1285-1291.
Rahman, et al. "The phosphorylated form of FTY720 activates PP2A, represses inflammation and is devoid of S1P agonism in A549 lung epithelial cells" *Sci. Rep.* 6:37297 (2016).
Reber, et al. "New models for analyzing mast cell functions in vivo" *Trends Immun.* 33 (2012) pp. 613-625.
Reines, et al. "Topical application of sphingosine-1-phosphate and FTY720 attenuate allergic contact dermatitis reaction through inhibition of dendritic cell migration" *J. Invest. Dermatol.* 129 (2009) pp. 1954-1962.
Ribatti, D. "Mast cells and macrophages exert beneficial and detrimental effects on tumor progression and angiogenesis" *Immun. Lett.* 152 (2013) pp. 83-88.
Rivera, et al. "The alliance of sphingosine-1-phosphate and its receptors in immunity" *Nat. Rev. Immun.* 8 (2008) pp. 753-763.
Rodriguez, et al. "Sphingosine-1-phosphate: a new modulator of immune plasticity in the tumor microenvironment" *Front. Oncol.* 6 (2016) pp. 1-16.
Rogers, et al. "Regulation of NF-κB activation and nuclear translocation by exogenous nitric oxide (NO) donors in TNF-α activated vascular endothelial cells" *Nitric Oxide* 16 (2007) pp. 379-391.
Saba, et al. "The BST1 gene of *Saccharomyces cerevisiae* is the sphingosine-1-phosphate lyase" *J. Biol. Chem.* 272 (1997) pp. 26087-26090.
Schaper, et al. "Sphingosine-1-phosphate exhibits anti-proliferative and anti-inflammatory effects in mouse models of psoriasis" *J. Dermatol. Sci.* 71 (2013) pp. 29-36.
Schwartz, et al. "Tryptase levels as an indicator of mast-cell activation in systemic anaphylaxis and mastocytosis" *N. Engl. J. Med.* 316 (1987) pp. 1622-1626. (Abstract only).
Sedivy, et al. "Short-term rhythmic proliferation of human breast cancer cell lines: Surface effects and fractal growth patterns" *J. Pathol.* 197 (2002) pp. 163-169.
Sehra, et al. "Mast cells regulate epidermal barrier function and the development of allergic skin inflammation" *J. Invest. Dermatol.* 136 (2016) pp. 1429-1437.
Siegel, et al."Diminished allergic disease in patients with STAT3 mutations reveals a role for STAT3 signaling in mast cell degranulation" *J. Aller. Clin. Immun.* 132 (2013) pp. 1388-1396.
Smith, et al. "Fractal methods and results in cellular morphology-dimensions, lacunarity and multifractals" *J. Neuro. Meth.* 39 (1996) pp. 123-136.
Sobel, et al. "FTY720 phosphate activates sphingosine-1-phosphate receptor 2 and selectively couples to $G\alpha_{12/13}$/Rho/Rock to induce myofibroblast contraction" *Mol. Pharma.* 87 (2015) pp. 916-927.
Spergel, et al. "Epicutaneous sensitization with protein antigen induces localized allergic dermatitis and hyperresponsiveness to methacholine after single exposure to aerosolized antigen in mice" *J. Clin. Invest.* 101 (1998) pp. 1614-1622.
Streba, et al. "A pilot study on the role of fractal analysis in the microscopic evaluation of colorectal cancers" *Rom. J. Morphol. Embry.* 56 (2015) pp. 191-196.

Suárez-Fariñas, et al. "RNA sequencing atopic dermatitis transcriptome profiling provides insights into novel disease mechanisms with potential therapeutic implications" *J. Aller. Clin. Immun.* 135 (2015) pp. 1218-1227.
Sulcova, et al. "Mast cells are dispensable in a genetic mouse model of chronic dermatitis" *Am. J. Pathol.* 185 (2015) pp. 1575-1587.
Sun, et al. "Topical application of fingolimod perturbs cutaneous inflammation" *J. Immun.* 196 (2016) pp. 3854-3864.
Szegedi, et al. "Cytokine profiles in interstitial fluid from chronic atopic dermatitis skin" *J. Eur. Acad. Derma. Venereol.* 29 (2015) pp. 2136-2144.
Thamrin, et al. "Fractals for physicians" *Paed. Resp. Rev.* 11 (2010) pp. 123-131.
Theoharides, et al. "Mast cells and inflammation" *Biochim. Biophys. Acta* 1822 (2012) pp. 21-33.
Valent, et al. "Clinical and laboratory parameters of mast cell activation as basis for the formulation of diagnostic criteria" *Int. Arch. Aller. Immun.* 156 (2011) pp. 119-127.
Voehringer, D. "Protective and pathological roles of mast cells and basophils" *Nat. Rev. Immun.* 13 (2013) pp. 362-375.
Walter, et al. "Digital image processing and analysis" *Video Microscopy* (S. Inoue, Ed.) Plenum Press (1986) pp. 327-392.
Wang, et al. "Skin microbiome promotes mast cell maturation by triggering stem cell factor production in keratinocytes" *J. Aller. Clin. Immun.* 139 (2017) pp. 1205-1216.
Wang, et al. "Repeated epicutaneous exposures to ovalbumin progressively induce atopic dermatitis-like skin lesions in mice" *Clin. Exp. Aller.* 37 (2007) pp. 151-161. (Abstract only).
Watanabe, et al. "Endotoxin contamination of ovalbumin suppresses murine immunologic responses and development of airway hyperreactivity" *J. Biol. Chem.* 278 (2003) pp. 42361-42368.
Wedman, et al. "A new image analysis method based on morphometric and fractal parameters for rapid evaluation of in situ mammalian mast cell status" *Microsc. Microanal.* 21 (2015) pp. 1-9.
Wernersson, et al. "Mast cell secretory granules: Armed for battle" *Nat. Rev. Immun.* 14 (2014) pp. 478-494.
Wick, et al. "Quantitative measurement of cell migration using time-lapse videomicroscopy and non-linear system analysis" *Histochem. Cell Bio.* 119 (2003) pp. 15-20.
Wolters, et al. "Tissue-selective mast cell reconstitution and differential lung gene expression in mast cell deficient $Kit^{W-sh}/Kit^{W-sh}$ sash mice" *Clin. Exp. Aller.* 35 (2005) pp. 82-88.
Wu, et al. "Mast cell FcεRI-induced early growth response 2 regulates CC chemokine ligand 1-dependent $CD4^+$T cell migration" *J. Immun.* 190 (2013) pp. 4500-4507.
Ying, et al. "High-affinity immunoglobulin E receptor (FcεRI)-bearing eosinophils, mast cells, macrophages and Langerhans' cells in allergen-induced late-phase cutaneous reactions in atopic subjects" *Immunology* 93 (1998) pp. 281-288.
Yoon, et al. "IL-23 induced in keratinocytes by endogenous TLR4 ligands polarizes dendritic cells to drive IL-22 responses to skin immunization" *J. Exper. Med.* 213 (2016) pp. 2147-2166.
Zhang, et al. "A three-dimensional fractal analysis method for quantifying white matter structure in human brain" *J. Neuro. Meth.* 150 (2006) pp. 242-253.
Zhu, et al. "Tryptase and protease-activated receptor-2 stimulate scratching behavior in a murine model of ovalbumin-induced atopic-like dermatitis" *Int. Immunopharm.* 28 (2015) pp. 507-512.
Zouien, et al. "Applying fractal dimension and image analysis to quantify fibrotic collagen deposition and organization in the normal and hypertensive heart" *Microsc. Microanal.* 20 (2014) pp. 1134-1144.

\* cited by examiner

SEQUENCE LISTING

<160> NUMBER OF SEQ ID NOS: 18

<210> SEQ ID NO 1
<211> LENGTH: 19
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1
cagaaggggc ggagatgat                                                 19

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aggccggtgc tgctgagtat gtc                                            23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
attgtgagtg ccaccgttca                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcagccaatc ttgcgttaca                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cactcacctg ctgctactca                                                20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcttggtgac aaaaactaca gc                                             22

<210> SEQ ID NO 7
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
gccatatgga gctgacaccc                                                      20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagtcaggaa aatgacacct ggc                                                  23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgtggacctc gagagtgaga a                                                    21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggcttgcta ggcgaaagaa g                                                    21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtgtatgag cttatcttcc agc                                                  23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgttgttcg atcttacgtc ca                                                   22

<210> SEQ ID NO 13
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 13
tacgggctga ttctcattcc c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtccaccaa tgggtagaag a                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacccactgg aatatcgacc c                                              21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagtctcaca acgggaggaa                                                20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgccctcacc atcatcctca ct                                             22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcggttcct tcgagtgaca                                                20
```

CULTURE SYSTEM AND MEDIA FOR SKIN EXPLANTS PROVIDING ENHANCED VIABILITY AND ENABLING MOLECULAR STUDIES

CROSS REFERENCE TO RELATED APPLICATION

This application claims filing benefit of U.S. Provisional Patent Application Ser. No. 62/751,765, having a filing date of Oct. 29, 2018, which is incorporated herein by reference in its entirety.

STATEMENT AS TO RIGHTS TO INVENTIONS MADE UNDER FEDERALLY SPONSORED RESEARCH

This invention was made with Government support under Contract No. R21 AR067996, awarded by the National Institutes of Health (NIH) and National Institute of Arthritis and Musculoskeletal and Skin Diseases (NIAMS). The Government has certain rights in the invention.

SEQUENCE LISTING

A Sequence Listing has been filed electronically in ASCII format and is hereby incorporated by reference in its entirety. Said ASCII copy, created on Jan. 2, 2020, is named USC-602_Sequence_List.txt and is 4,406 bytes in size.

BACKGROUND

In vitro studies on various types of living tissue is essential to cellular and molecular research. Human skin explant cultures are particularly important because they provide a safe and effective method of studying numerous skin conditions, in part because explants contain mast cells. Mast cells are long-lived tissue-dwelling cells found in all vascularized tissues and they serve as a model cell for immunomodulatory functions in many physiological processes because of the vast repertoire of mediators they release upon activation. Mast cells are especially valuable in the study of dermatology, allergy, inflammation, and cancer.

For effective study in human models, skin explants must remain capable of being used in various cellular and molecular studies for up to and past seven days. The current state of cell culture media fails to provide an environment that is both conducive for various studies and that allows the explants to remain viable for testing up to and past the seven-day threshold. Partially due to their short life span, most preliminary mast cell studies from human explants remain in animal models. Pre-clinical animal models are expensive, and the results are not directly applicable to human treatment. Since the results are not directly applicable to humans, human studies must follow the animal models to validate the treatment's success and safety, which adds to the expense and time.

Human skin explants are readily attainable through various tissue networks. In addition, Institutional Review Board ("IRB") exemption 4 allows for the circumvention of animal studies when using deidentified human samples. By extending the life span of human skin explants in vitro and replicating an environment conducive for various treatments, researchers may circumvent the need for animal models reducing both the cost and time of mast cell studies.

Specifically, a culture system for human skin explants should extend cell life to seven days or more. The system should also allow for conducting various cellular and molecular studies including, but not limited to, gene and molecular expression assays following exposure to different chemicals or antigens.

There is also a need to develop cell culture systems and media for human skin explants that allow for extended viability of mast cells. Further, there is a need for a cell culture system that easily allows for various cellular and molecular studies including, but not limited to, identification of mast cells and their activation status (gene and molecular) upon exposure of the epidermis layer of the skin to different chemicals or antigens.

SUMMARY OF THE INVENTION

Embodiments of the invention include systems and media for mammalian cell culture that enhance cell viability, which enables biological assays and quantitative studies in tissues such as skin explants. Certain embodiments may be used in coordination with each other or may be practiced separately. An exemplary embodiment of the invention is a culture medium that includes Dulbecco's Modified Eagle's Medium, X-VIVO™ serum free medium, and subcutaneous adipocyte medium. In one embodiment, the culture medium includes approximately 30-60% Dulbecco's Modified Eagle's Medium by volume, approximately 30-60% X-VIVO™ serum free medium by volume, and approximately 2.5-15% subcutaneous adipocyte medium by volume. Certain embodiments of the culture medium can also include recombinant human stem cell factor. Embodiments of the invention disclosed here are not limited to the manufactured components that are recited and can encompass equivalents, as well as combinations, of the individual chemical components that make up the compositions described herein.

Another exemplary embodiment of the invention is a culture system which employs a culture medium that includes Dulbecco's Modified Eagle's Medium, X-VIVO™ serum free medium, and subcutaneous adipocyte medium. In embodiments of the culture system, the culture medium partially immerses a mammalian skin explant located within a container or a vessel. As specified above, different volumetric ratios of the individual components may be used to produce the culture medium providing various alternative embodiments of the culture system. Additionally, embodiments of the culture system can include recombinant human stem cell factor as part of the culture medium providing further alternative embodiments of the culture system.

Embodiments of the cell culture system may also include a vessel that provides a controlled region, area, or chamber. In an exemplary embodiment, the vessel includes a humidified chamber that is configured to maintain a temperature and a $CO_2$ concentration. In certain embodiments, the culture system is configured to maintain a temperature of approximately 25-43° C. and a $CO_2$ concentration of about 0-12% by volume. In some embodiments, the culture system can be configured to adjust the temperature and/or $CO_2$ concentration during cell culture to either maintain the attribute at an approximately constant value or change the attribute over time.

Another embodiment of the cell culture system includes a port. The port provides access to the vessel so that new media may be added to the vessel or old media removed during the time the cell culture system is in use.

In an exemplary embodiment of the cell culture system, a culture medium is provided to the vessel such that the culture medium partially immerses a mammalian skin explant in the vessel. In one embodiment, the cell culture medium immerses all skin layers except the outermost layer, the epidermis. The temperature and $CO_2$ concentration in the vessel are maintained at approximately 37° C. and 5%, respectively.

In certain embodiments, the culture system can further include an explant cover. The explant cover is placed over the mammalian skin explant to cover a portion of the mammalian skin explant that is not immersed in the culture medium. This explant cover can be made from a variety of materials, such as fibrous materials, plastics, or composites. Further, the explant cover may be used to provide a chemical to the mammalian skin explant. The explant cover may also provide a controlled barrier between the exposed portion of the mammalian skin explant and the vessel. In certain embodiments, the explant cover can be a fibrous material such as a sterile gauze pad. Further, this gauze pad can include an antigen, such as ovalbumin antigen, which can be used to stimulate an immune response in the mammalian skin explant.

Practicing the embodiments of the disclosure, it is possible to keep a mammalian skin explant, such as a human skin explant, viable for at least 3 days. Certain embodiments may keep a mammalian skin explant viable for at least 7 days. Yet other embodiments may keep mammalian skin explants viable for at least 4, 5, 6, 8, 9, 10, 11, 12, or more than 16 days by using a culture system as described herein.

An exemplary embodiment of the invention is a method of performing an in vitro study on a mammalian skin explant using a culture system as substantially described in the above embodiments. For these in vitro studies, the mammalian explant is analyzed, or the culture medium is analyzed, after the mammalian skin explant remains viable in culture or in a culture system for a time span. Many different types of in vitro studies may be used with the compositions, systems and methods describe herein; two exemplary in vitro studies are an mRNA analysis and a protein analysis. Conducting an mRNA analysis may include running quantitative real time polymerase chain reaction (qrt-PCR), which can be done using a variety of protocols. Alternatively, conducting a protein analysis may include running a Western blot which can be done using a variety of protocols. Example protocols are provided in the Detailed Description; however, these protocols are provided for illustrative purposes and are not meant to limit the scope of techniques and conditions which can be practiced with embodiments of the disclosure.

In certain embodiments, the method of performing an in vitro study on a mammalian skin explant uses a human skin explant. Human skin explants can be obtained from a variety of sources, such as mastectomies and abdominoplasties. Further, these human skin explants may include all layers of the dermis or only a portion of the layers and can be approximately 2-15 mm in thickness. In some embodiments, the human skin explant may be prepared before performing an in vitro study or before use in the culture system. This preparation can include punch biopsies to modify the size and shape of the human skin explant, shaving, and/or tape stripping.

As described herein, embodiments of the invention can provide a method for performing in vitro studies on mammalian skin explants after the mammalian skin explants remain viable for at least the time span of 3 days. In some embodiments, the in vitro studies may be conducted after the mammalian skin explants remain viable for at least the time span of 7 days. Thus, it is contemplated that embodiments of the disclosure when used in conjunction, or on their own, can provide methods for performing in vitro studies on mammalian skin explants, such as human skin explants, after the mammalian skin explants remain viable for at least the time span of 3, 4, 5, 6, 7, 8, 9, 10, 11, 12, 13, 14, 15, 16, or greater than 16 days.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 3a illustrates a Western blot gel that is stained for the STAT3 protein (STAT3) or the phosphorylated STAT3 protein (p-STAT) using skin biopsy samples from 3 different patients and prepared as described herein. FIG. 3b illustrates a graph showing the fold increase of p-STAT3 to STAT3 for skin explants treated with an OVA patch compared to a saline patch.

FIG. 5 illustrates an exemplary method whereby a stained skin section [A] is magnified to isolate and clean an image of the epidermis [B]. An equation [C] can then be applied to the cleaned image to determine an average thickness [D].

FIG. 6 shows microscopy sections of cultured human explants stained with methylene blue after exposure to an OVA patch during culture (right) or a saline patch during culture (left).

FIG. 7 compares mast cell activation (degranulation) between explant samples exposed to an OVA patch during culture or a saline patch during culture.

Figure 1:
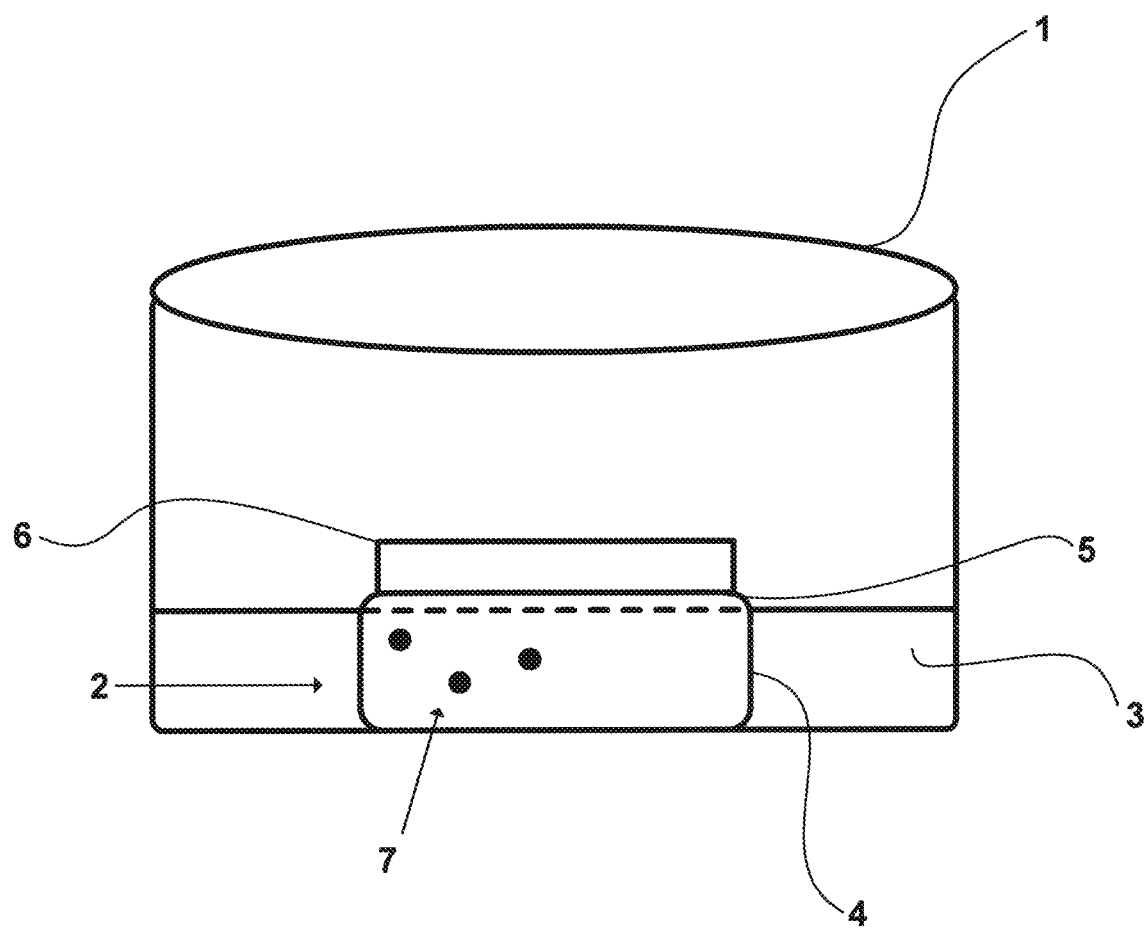
FIG. 1 illustrates an exemplary embodiment of the disclosure which shows a vessel 1 containing a skin biopsy sample 2 that is partially immersed in a cell culture medium 3. The skin biopsy sample includes an under-skin layer 4 which is immersed in the cell culture medium 3 and a top-skin layer 5 (e.g., epidermis) in contact with a cover 6. The skin biopsy sample contains many cells including mast cells 7.

Repeat use of reference characters in the present specification and drawings is intended to represent the same or analogous features or elements of the present invention.

DETAILED DESCRIPTION

Reference will now be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally speaking, the present invention is directed to a human cell culture medium that can allow for the identification of mast cells, important cells in allergy, inflammation and cancer, and their activation status upon exposure of the epidermis layer, or the outer most layer of the skin, to different chemicals. This medium also allows for the conduction of gene and molecular expression analyses in human biopsies after exposure to different chemicals. Various features of the cell culture medium of the present invention are discussed in more detail below.

Specifically, embodiments of the culture medium may include approximately 30-60% Dulbecco's Modified Eagle's Medium by volume, approximately 30-60% X-VIVO™ serum free medium by volume, and approximately 2.5-15% subcutaneous adipocyte medium by volume. Further, certain embodiments of the culture medium can also include recombinant human stem cell factor. Embodiments of the culture system can include embodiments of the culture medium such as a culture medium that includes approximately 30-60% Dulbecco's Modified Eagle's Medium by volume, approximately 30-60% X-VIVO™ serum free medium by volume, and approximately 2.5-15% subcutaneous adipocyte medium by volume. Certain embodiments of the culture system can also include recombinant human stem cell factor as part of the culture medium. For embodiments that include recombinant human stem cell factor, the recombinant human stem cell factor can be present in an amount ranging from about 100 ng/mL to about 300 ng/mL, such as from about 125 ng/mL to about 275 ng/mL, or from about 150 ng/mL to about 250 ng/mL, based on the volume of X-VIVO™ serum free medium. Embodiments of the culture system may further comprise a vessel for controlling temperature and pressure. In certain embodiments, the culture system is configured to maintain a temperature of approximately 25-43° C. and a $CO_2$ concentration of about 0-12% by volume.

Several exemplary embodiments of culture conditions are provided in Table 1 which shows ranges for the culture system conditions: temperature and $CO_2$ concentration. Table 1 also shows ranges for the culture medium components: Dulbecco's Modified Eagle's Medium (DMEM), X-VIVO™ serum free medium (X-VIVO™), subcutaneous adipocyte medium (Subc. Adipocyte), and recombinant human stem cell factor (Recomb. h-Stem Cell factor). Ranges of the culture medium components can be used in combination with embodiments of the culture system as described herein.

TABLE 1

Exemplary ranges for embodiments of the culture system and the culture medium.

| Culture system conditions | | Culture medium components | | | |
|---|---|---|---|---|---|
| Temperature ° C. | $CO_2$ % vol | DMEM % vol | X-VIVO % vol | Subc. Adipocyte. % vol | Recomb. h-Stem Cell factor ng/mL X-VIVIO |
| 25-43 | 0-12 | 30-60 | 30-60 | 2.5-15 | 100-300 |
| 20-44 | 1-10 | 35-55 | 35-55 | 5-12.5 | 125-275 |
| 30-39 | 2-8 | 40-50 | 40-50 | 7.5-10 | 150-250 |

As an example, for illustrative purposes, a culture medium could be formulated which includes approximately 45.45% DMEM, 45.45% X-VIVO™, and 9.09% subcutaneous adipocyte medium. This medium could be used alone, or it could also include recombinant human stem cell factor at a concentration of 200 ng/mL based on the volume of X-VIVO™. Embodiments of the culture system could employ the example culture medium at different culture conditions. To illustrate an example culture system, the culture medium could be held at 37° C. at a 5% $CO_2$ concentration.

Additionally, embodiments of the culture medium and culture system can further include supplements to one or more of the components. Possible supplements can include additional salts, buffers, amino acids, and/or antibiotics. For embodiments that include a supplemented component, the volume percent of the culture medium component can be calculated based on the supplemented composition, rather than the amount of the component. In some embodiments, the DMEM can be supplemented with 12-25% heat-inactivated fetal bovine serum. In some embodiments, the DMEM can be supplemented with HEPES buffer to a concentration of 0.5 mM to 3 mM. In some embodiments, the DMEM can be supplemented with L-glutamine to a concentration of 2-6 mM. In some embodiments, the DMEM can be supplemented with sodium pyruvate to a concentration of 0.5 mM to 3 mM. In some embodiments, the DMEM can be supplemented with penicillin and/or streptomycin to a concentration of penicillin 2,000-14,000 International Units/milliliter and streptomycin 4,000-15,000 micrograms/milliliter. In certain embodiments, the DMEM can be supplemented with one or more of the additional supplements provided in this disclosure. For example, a DMEM component used in culture medium or system could be prepared by supplementing Dubelco's Modified Eagle's Medium with 20% heat-inactivated fetal bovine serum, 2 mM HEPES, 4 mM L-glutamine, 2 mM sodium pyruvate, and 2% antibiotic solution (penicillin 10,000 International Units/milliliter and streptomycin 10,000 micrograms/milliliter). The supplemented DMEM can then be used as a component in the culture system or culture medium in an amount of approximately 30 to 60 vol %.

For embodiments of the disclosure that include recombinant human stem cell factor, the recombinant human stem cell factor can be added directly to the culture medium or can be added as a supplement to one or more of the components. For example, recombinant human stem cell factor can be added to the X-VIVO™ component at a concentration of 200 ng/mL to produce a supplemented X-VIVO™ which can then be used as a component of the culture medium. In embodiments of the disclosure, the recombinant human stem cell factor can be added to the X-VIVO™ component at a concentration of 100-300 ng/mL. In particular, the recombinant human stem cell factor can be added at a concentration of 125-275 ng/mL based on the volume of X-VIVO™. In certain embodiments, the recombinant human stem cell factor can be added to the X-VIVO™ component at a concentration of 150-250 ng/mL.

Embodiments of the culture system or methods that use a culture system as described herein may further include an explant cover 6. The explant cover can comprise a matrix, and in some cases, an antigen such as ovalbumin. In an embodiment, the matrix can be submerged in a solution containing the antigen. As an example, the matrix can be submerged in a solution containing 1-10 mg/mL ovalbumin antigen. Alternative antigens or irritants may be used at different concentrations to elicit different immune responses, such as an allergic response when using pollen, animal dander or saliva, or nut proteins.

FIG. 1 illustrates an embodiment of the culture system. The culture system includes a vessel 1 that contains the mammalian skin explant 2 which is partially immersed in a culture medium 3. In the embodiment illustrated, an explant cover 6 is shown covering a portion of the mammalian skin explant 2. In some embodiments, the explant cover can include a chemical compound such as an antigen that would stimulate activation of mast cells 7. The vessel provides a controlled environment; alternatively, the vessel can be placed in a controlled environment such that the temperature and $CO_2$ concentration can be regulated. Additionally, embodiments of the culture system can enable a method for conducting in vitro studies on a mammalian skin explant 2 that has remained viable for at least 7 days. Examples of these studies and the corresponding data may be found in the discussion below along with the remaining Drawings.

Figure 2:
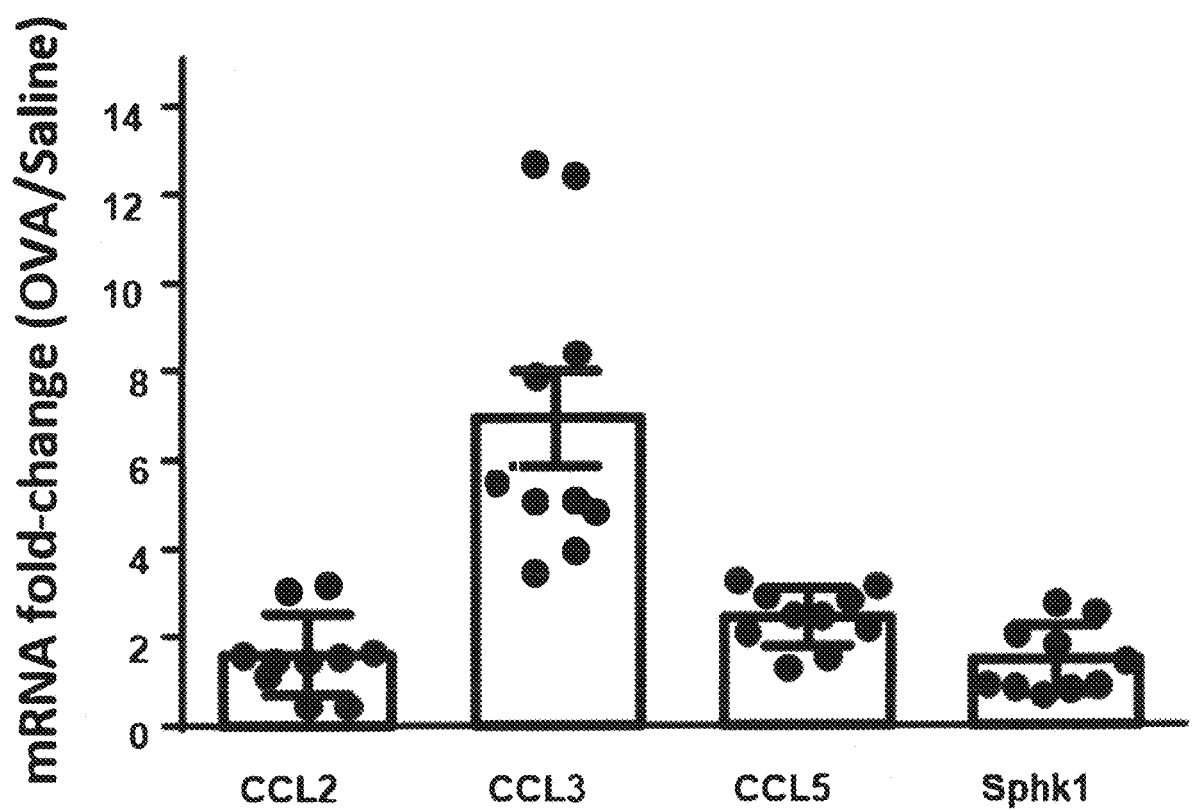
FIG. 2 illustrates an exemplary mRNA analysis using human skin explants prepared as described by methods and systems herein. The graph shows increased mRNA expression of chemokines CCL3 and CCL5, as well as sphingosine kinase (Sphk)1. The data shows a seven-day exposure to ovalbumin antigen (OVA) when compared to a seven-day exposure to saline, where a sample of size of n=5 was used and qrt-PCR testing was completed in duplicate.

FIG. 2 illustrates an exemplary mRNA in vitro analysis showing increased mRNA expression of chemokines CCL3 and CCL5, as well as sphingosine kinase (Sphk)1, in human skin explants cultured as described herein (see Methods) after a seven-day exposure to OVA when compared to a seven-day exposure to saline. A test sample size of n=5 was used a qrt-PCR testing was completed in duplicate.

Figure 3A:
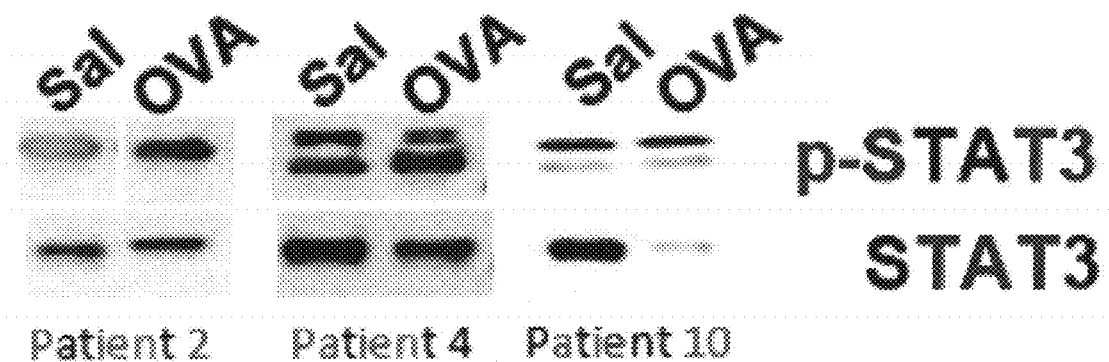
FIG. 3a and FIG. 3b illustrate an exemplary protein analysis using human skin explants prepared as described by methods and systems herein.
Figure 3B:
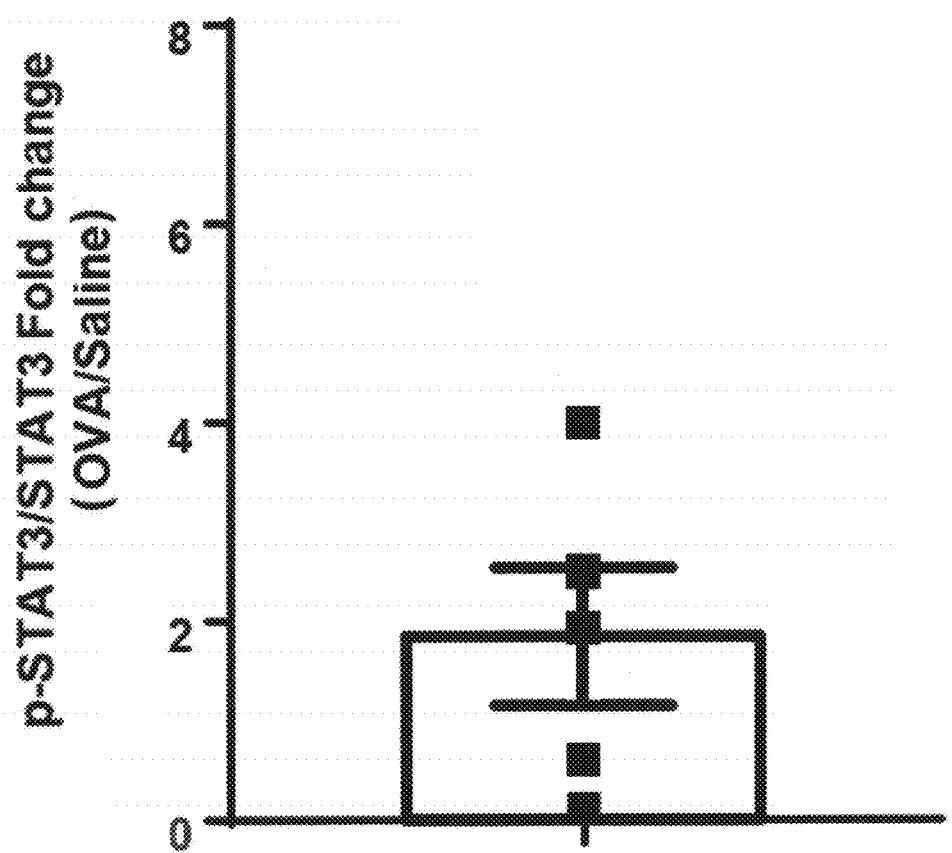

FIG. 3a illustrates an exemplary protein in vitro analysis. The Western blot gel shows a numerical (but not statistically significant) increase in STAT3 activation to produce the phosphorylated protein (p-STAT3) after seven days exposure to an OVA patch when compared to seven days exposure to a saline patch. Skin explants from five different human female donors were cultured (see Methods), and after 7 days, the skin explants were removed from culture and used to run a Western blot (see Procedures—Protein Analysis). FIG. 3b shows a graph quantifying the data from FIG. 3a.

Figure 4A:
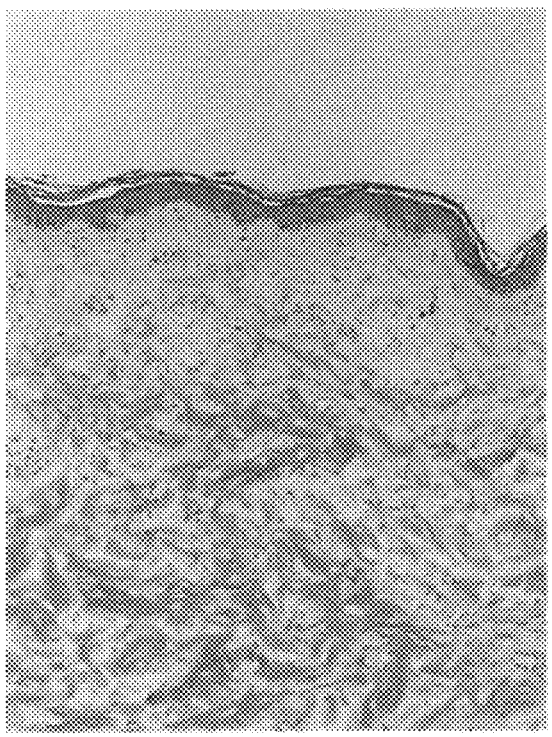
FIG. 4a and FIG. 4b illustrate an exemplary in situ skin section analysis using human skin explants prepared as described by methods and systems herein.
Figure 4B:

FIGS. 4a-4b show microscopy sections taken from human skin explants cultured as described herein (see Methods). FIGS. 4a and 4b show images demonstrating preservation of skin structural architecture after seven days exposure to a saline patch or an OVA patch, respectively. The microscopy sections have been stained using Hematoxylin and Eosin (H & E) staining and the scale bar in the lower left corner measures 200 μm.

Figure 5:
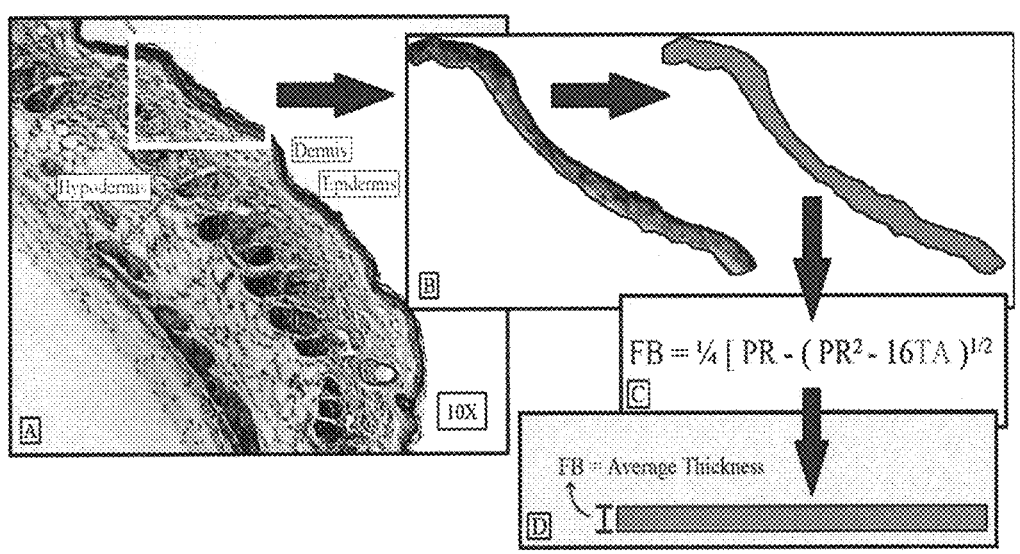
FIG. 5 illustrates an alternative in situ skin section analysis using human skin explants prepared as described by methods and systems herein.

FIG. 5 shows a method of determining the average epidermis thickness of a mammalian skin explant. In FIG. 5 the image in [A] shows an H & E stained cross section of mouse skin labeled with the different skin tissue layers. Image software can be used to isolate the region for the epidermis as shown in [B]. This image can be used to calculate the fiber breadth (FB) by using the equation shown in [C] which provides an approximation of the average thickness of the skin layer shown in [D]. These steps are applied to an image of a mouse skin explant. The same methodology could be applied to other mammalian skin explants, such as human skin explants, which have been cultured using embodiments of the media, systems, and methods detailed herein.

Figure 6:
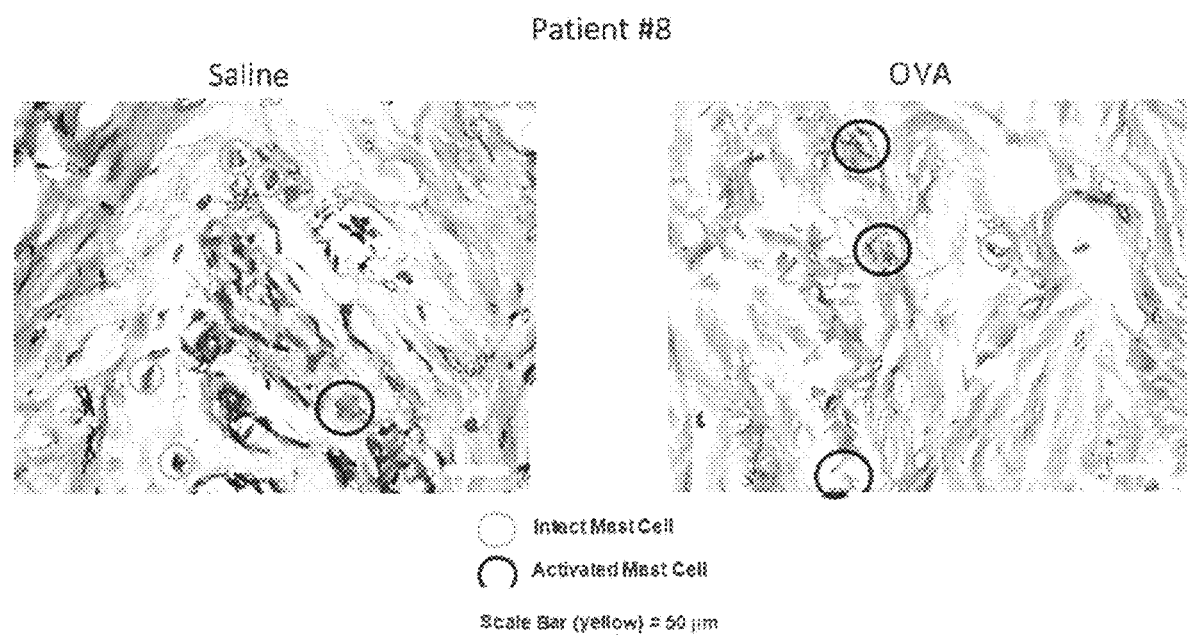
FIG. 6 illustrates an exemplary mast cell activation status analysis using human skin explants prepared as described by methods and systems herein.

FIG. 6 shows an example analysis for determining mast cell activation status in mammalian skin explants. The microscopy sections shown were obtained from human skin explants cultured as described herein (see Methods) for 7 days using a saline patch (left) or an OVA patch (right). FIG. 6 shows a comparison of human skin explants stained with methylene blue. Activated mast cells are identified in dark gray circles and intact mast cells are identified in light gray circles. The images demonstrate a statistically significant increase in mast cell activation (degranulation) when using a culture system that includes an OVA patch, compared to a culture system that includes a saline patch.

Figure 7:
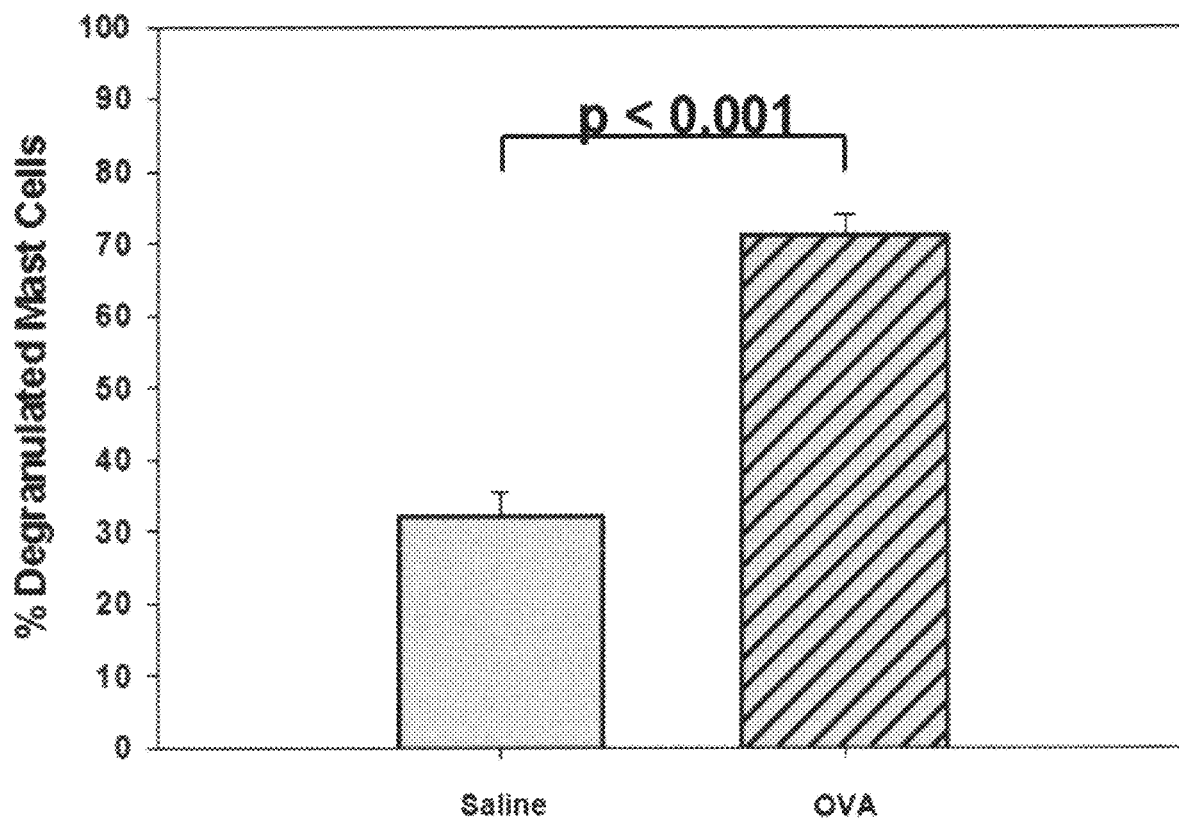
FIG. 7 illustrates a graph quantifying mast cell activation status as determined by exemplary methods herein.

FIG. 7 shows a graph that quantifies the mast cell activation status images provided in FIG. 6. The graph shows the % Degranulated Mast Cells, which can be determined through imaging software or manual counting, of microscopy sections from human explants. Quantified data was obtained from 40 images, using 4 female human subjects with 10 images taken per subject.

Example 1

Example 1 discusses various methods and procedures and provides exemplary embodiments that may be understood in conjunction with the Drawings and Description provided herein.

Methods

Sample Preparation

Fresh human skin biopsies were obtained from mastectomies and abdominoplasties from the Cooperative Human Tissue Network, an NCI supported source. Ten-mm full-thickness human skin explant samples were isolated with sterile punchers (Acuderm Inc.; Fort Lauderdale, FL) from human biopsies after shaving and tape-stripping.

System and Culture Preparation

The 10 mm human skin explant samples were placed in a 24-well tissue culture plate for immersion of all skin layers but the outermost one in 45% Dulbecco's Modified Eagle's Medium (Corning Inc.; Corning, New York), 45% X-VIVO™ serum free medium (Lonza; Walkersville, MD) supplemented with 200 ng/mL recombinant human stem cell factor (PeproTech US; Rocky Hill, NJ), and 10% subcutaneous adipocyte medium (ZenBio; Research Triangle Park, NC) (FIG. 1). The skin surface was then covered with a sterile circular gauze patch (FIG. 1) containing ovalbumin ("OVA") antigen (Sigma Aldrich; St. Louis, MO) or saline as a control.

The tissue culture plates were then placed in a 37° C. and 5% $CO_2$ humidified incubator for 7 days. After 7 days, the human skin explant samples were split. One half of the explant samples were processed for fixation and paraffin block preparation. The other half of the explant samples was further split, one half was used for mRNA analysis and the other half was used for protein analysis.

Procedures mRNA Analysis mRNA analysis was used to determine the activity of CCL2, CCL3, CCL5 and sphingosine kinase (Sphk)1 in human skin explants following a seven-day culture with exposure to an OVA patch or a saline patch. Skin explants were prepared as described above (see Sample preparation). After the seven-day treatment, a quarter of the human skin explants were snap-frozen in liquid nitrogen and stored at −80° C. until use.

RNA isolation was performed on the snap-frozen explants. Each explant was homogenized to produce a homogenized sample. The samples were lysed by adding 700 µL of QIAzol Lysis reagent to each sample. The reagent was mixed by vortexing or pipetting up and down until the mixture was well homogenized. At this point, the samples could be stored in QIAzol reagent at −80° C. or the samples could proceed to RNA extraction.

Then, RNA extraction was performed. If frozen, samples defrosted at room temperature for 5 minutes. 140 µL of chloroform was added to each tube and cap was secured. Each tube was vigorously shaken for 15 seconds. Each tube was left at room temperature for 5 minutes. After 5 minutes, tubes were centrifuged for 15 minutes at 12,000×g at 4° C. The upper aqueous phase was transferred to a new collection tube (Qiagen miRNeasy® Mini Kit; Hilden, Germany) using a 200 µL pipette tip. The exact volume of each sample was measured, and 1.5 volumes of 100% ethanol added accordingly. Ethanol was mixed by pipetting up and down several times. No centrifugation was performed, and the following steps proceeded with no delay between. 700 µL of the sample was pipetted into a RNeasy® Mini spin column (Qiagen miRNeasy® Mini Kit; Hilden, Germany) that was in a 2 mL collection tube (Qiagen miRNeasy® Mini Kit; Hilden, Germany). The tube was centrifuged at 8,000×g for 15 seconds at room temperature. Flow through was discarded. This step was repeated by pipetting the remainder of sample into the same spin column and centrifuging for 15 seconds at 8,000×g. 350 µL of RWT buffer (Qiagen miRNeasy® Mini Kit; Hilden, Germany) was then added to the tube. Following, the tube was centrifuged for 15 seconds at 8,000×g at room temperature to wash the column. Flow through was discarded. In advance, DNase mix was prepared containing 10 µL of DNase (Qiagen RNase-Free DNase; Hilden, Germany) per 70 µL of RDD buffer (included in the Qiagen RNase-Free DNase set). DNase mix was added directly onto the mesh of the RNeasy® Mini spin column (Qiagen miRNeasy® Mini Kit; Hilden, Germany) and was left to sit for 15 minutes at room temperature. On top of the mesh of each RNeasy® Mini spin column, 350 µL of RWT buffer (Qiagen miRNeasy® Mini Kit; Hilden, Germany) was added. Then the column was centrifuged for 15 seconds at 8,000×g at room temperature and flow through was discarded. To each, RNeasy® Mini spin column 500 µL of RPE buffer (Qiagen miRNeasy® Mini Kit; Hilden, Germany) was added. Columns were centrifuged for 15 seconds at 8,000×g at room temperature. The old collection tubes with the flow through were discarded. Another 500 µL of RPE buffer (Qiagen miRNeasy® Mini Kit; Hilden, Germany) was added to each RNeasy® Mini spin column and then centrifuged for 2 minutes at 8,000×g at room temperature. Carefully and without touching the flow through, the RNeasy® Mini Spin columns were transferred into new collection tubes with no lid and then centrifuged at full speed for 1 minute at room temperature. The old collection tubes with the flow through were discarded. The RNeasy® Mini spin column was again transferred into another set of new collection tubes with no lid. Carefully, 50 µL of RNase-free water (Qiagen miRNeasy® Mini Kit; Hilden, Germany) was pipetted on top of the mesh and was left to sit for 2 minutes before centrifuging for 1 minute at 8,000×g at room temperature to elute the RNA. The first eluate of RNA and transfer was collected on top of the mesh again and left to sit for 2 minutes before centrifuging for 1 minute at 8,000×g at room temperature. RNA was transferred into tubes with lids and left on ice until concentration determination.

Final RNA concentration was found by determining the ratio of absorbance at 260 nm versus 230 and 280 nm using a NanoDrop spectrophotometer (Thermo Fisher; Waltham, MA). Usual yield was 5-15 µg of RNA per sample.

Next, cDNA was synthesized using the iScript™ cDNA synthesis kit (Bio-Rad; Hercules, CA). 1 µg of RNA was added to an Eppendorf tube and placed immediately on ice. The reaction mix was brought up to 15 µL using Nuclease-free water (Bio-Rad; Hercules, CA). Then 4 µL of 5× iScript™ reaction mix (Bio-Rad; Hercules, CA) and 1 µL of iScript™ (Bio-Rad; Hercules, CA) was added bringing the total reaction mixture to 20 L. The reaction mix was incubated for 5 minutes at 25° C., then at 42° C. for 30 minutes, and then at 85° C. for 5 minutes. Samples could then be held at 4° C. or stored at −20° C.

Once the cDNA was synthesized the qrt-PCR reaction was run. The following primers were used for qrt-PCR amplification: GAPDH forward primer CAGAAGGGGCG-GAGATGAT (SEQ ID NO: 1) and reverse primer AGGCCGGTGCTGCTGAGTATGTC (SEQ ID NO: 2); FCFR1a forward primer ATTGTGAGTGCCACCGTTCA (SEQ ID NO: 3) and reverse primer GCAGC-CAATCTTGCGTTACA (SEQ ID NO: 4); CCL2 forward primer CACTCACCTGCTGCTACTCA (SEQ ID NO: 5) and reverse primer GCTTGGTGACAAAAACTACAGC (SEQ ID NO: 6); CCL3 forward primer GCCATATG-GAGCTGACACCC (SEQ ID NO: 7) and reverse primer TAGTCAGGAAAATGACACCT GGC (SEQ ID NO: 8); Sphk1 forward primer CGTGGACCTCGAGAGTGAGAA (SEQ ID NO: 9) and reverse primer AGGCTTGCTAGGCGAAAGAAG (SEQ ID NO: 10); Sgpl1 forward primer GGTGTATGAGCTTATCTTCC AGC (SEQ ID NO: 11) and reverse primer CTGTTGTTCGATCT-TACGTCCA (SEQ ID NO: 12); Sgpp1 forward primer TACGGGCTGATTCTCATTCCC (SEQ ID NO: 13) and reverse primer GGTCCACCAATGGGTAGAAGA (SEQ ID NO: 14); Sgpp2 forward primer CACCCACTG-GAATATCGACCC (SEQ ID NO: 15) and reverse primer AAGTCTCACAACGGGAGGAA (SEQ ID NO: 16); and CCL5 forward primer TGCCCTCACCATCAT CCTCACT (SEQ ID NO: 17) and reverse primer GGCGGTTCCTTCGAGTGACA (SEQ ID NO: 18). Primers were purchased from Thermo Fisher Scientific, Inc. (Waltham, MA). Individual PCR reaction mix stock solution was prepared for each primer using SensiFAST™ SYBR® No-ROX Kit (Bioline; Toronto, CA): 10 µL of SensiFAST™ SYBR® No-ROX Kit mix (2×) (Bioline; Toronto, CA), 500 nM (final concentration) of each forward and reverse primer, and 200 ng (final concentration) of cDNA template. The reaction mixture was brought to a final volume of 20 μL with nuclease-free water (Ultrapure Grade). The plate was sealed and centrifuged at 1,500 rpm for 5 minutes at room temperature to get rid of the air bubbles. The plate was then transferred to a real-time qPCR cycler machine (Bio-Rad CFX Connect; Hercules, CA). The real-time qPCR conditions were as follows: initial step at 95° C. for 5 minutes and cycles (n=40) consisted of 10 seconds at 95° C., followed by 1-minute annealing at 55° C. and extension at 72° C. All reactions were performed in duplicate. Data was analyzed with CFX Manager™ Software (Bio-Rad; Hercules, CA) to determine the threshold cycle value. Data was normalized to saline-treated samples and directly proportional to the amount of target gene mRNA relative to the amount of reference gene, GADPH mRNA levels.

Protein Analysis

A western blot analysis was used to determine whether there was an increase in STAT3 activation after a seven-day exposure to OVA when compared to a seven-day exposure to saline in human skin explants. Skin explants were prepared as described above (see Sample preparation). Activation of STAT3 was indicated through protein phosphorylation, p-STAT3 represents active protein and STAT3 represents inactive protein.

Snap-frozen samples were homogenized and prepared for western blot protein analysis. The samples were lysed with 120-180 μL of lysis buffer which contained: RIPA buffer (1×) (Thermo Scientific; Waltham, MA) supplemented with 0.2 mM sodium orthovanadate ($Na_3VO_4$) and Protease Inhibitor Cocktail at 1:500 dilution (Sigma Aldrich; St. Louis, MO). Each sample was sonicated (Qsonica 4422 Q55 Sonicator microprobe 1/8"; Newton, CT) three times on ice for 10 seconds with 1-minute intervals at an amplitude intensity of level 10. Samples were kept on ice for 15 minutes to yield a homogenous suspension. This suspension was used for analysis as whole cell lysate. Protein concentration of whole cell lysate was measured using Bradford technique: protein assay dye (Bio-Rad; Hercules, CA), VWR cuvettes PS semi-micro (VWR; Radnor, PA), and Beckman Coulter DU 800 spectrophotometer (Beckman Coulter; Brea, CA). The Bradford technique yielded on average three to four milligrams of protein per milliliter/sample.

Next, the western blot analysis was performed. The basic equipment included: Mini-PROTEAN Electrophoresis System (Bio-Rad; Hercules, CA), Mini Trans-Blot Cell (Bio-Rad; Hercules, CA), and Mini-PROTEAN TGX Gels (Bio-Ran; Hercules, CA). For detection in whole cell lysate, 9-12 μg of protein was loaded per sample per well. For one gel, electrophoresis started at 60 V for the first 20 minutes and then increased to 100 V. The running buffer used was Tris/Glycine/SDS Buffer (Bio-Rad; Hercules, CA). Proteins were transferred at 100 V after 1 hour onto a nitrocellulose membrane (Bio-Rad; Hercules, CA). The transfer buffer used comprised: 25 mM tris base, 192 mM glycine, pH 8.3, and 20% methanol. The membrane was then blocked for 40 minutes to an hour while rocking on a shaker at room temperature. The blocking buffer comprise wash buffer supplemented with 5% milk, Blotting-Grade Blocker (Bio-Rad; Hercules, CA). Following blocking, the buffer was washed three times for 10 minutes each wash using wash buffer while rocking at room temperature. The membrane was cut at the appropriate molecular weight based on the migration of protein markers. The membrane was then left overnight at 4° C. while gently shaking with the following primary antibodies: pStat3 diluted 1:200, Stat3 diluted 1:500, and GAPDH diluted 1:3,000 (pStat3, Santa Cruz Biotechnology, cat #sc-81523, Dallas, Texas; Stat3, Cell Signaling, cat #4904, Danvers, MA; and GADPH, Cell Signaling, cat #2188, Danvers, MA). The next day the membrane was washed with wash buffer three times for 10 minutes. Following the wash, the membrane was incubated with the secondary antibodies: pStat3 diluted 1:2,000 and Stat3 diluted 1:2,000 (pStat3, Santa Cruz Biotechnology, cat #sc-2055, Dallas, Texas; Stat3, Cell Signaling, cat #7072, Danvers, MA). The membrane was then washed three times for 10 minutes in wash buffer. Then the membrane was rinsed with deionized water three times. The membrane was then soaked for 2-3 minutes in SuperSignal™ West Pico Chemiluminescent substrate (Thermo Scientific; Waltham, MA). The membrane was then exposed to film using an automated X-Ray film processor. Band quantitation was carried out using ImageJ (National Institutes of Health). Integrated density numbers (in pixels) of p-Stat3 were normalized to total Stat3.

Results

Results provided in the drawings and described herein are meant to be exemplary and are not intended to limit the methods and compositions to modifications or alternatives as would be understood by a person of ordinary skill in the field of endeavor. Quantification of the data provided in FIG. 2 is provided below in Table 2.

TABLE 2

| mRNA analysis | | | | |
|---|---|---|---|---|
| mRNA | CCL2 | CCL3 | CCL5 | SphK1 |
| Fold change ± SEM (OVA/Saline) | 1.59 ± 0.29 | 6.92 ± 1.06 | 2.43 ± 0.20 | 1.48 ± 0.24 |
| P value Compared to saline (tow-tailed un-paired t-test) | P = 0.0548 | p < 0.0001 | P < 0.0001 | P < 0.0001 |

This data shows that human skin explants demonstrated statistically significant increases in chemokines CCL3 and CCL5, as well as an increase in sphingosine kinase (SphK1), following a seven-day exposure to OVA compared to saline. The data demonstrates that an analytical method for the detection of mRNA can be applied to human explants cultured for 7 days using the culture media, culture systems, and methods described herein.

Further, FIGS. 3a and 3b illustrate a western blot analysis of STAT3 phosphorylation following a seven-day exposure to OVA compared to saline. ImageJ was used to quantify the band intensity shown in FIG. 3a. This quantification shows a numerical increase in STAT3 activation with OVA compared to the saline control as shown below in Table 3. Together, these figures and the corresponding data quantification again demonstrate that an analytical method for the detection of cellular proteins can be applied to human skin explants cultured for 7 days.

TABLE 3

| protein analysis | |
|---|---|
| Western blot | p-STAT3/STAT3 |
| Fold change±SEM (OVA/Saline [Sal]) | 1.846 ± 0.62 |
| P value | P = 0.2095 |

FIGS. 4a-4b show that human skin explants cultured in the cell culture and culture systems described herein preserve their skin architecture following a seven-day culture, which supports that explant viability can be maintained in culture; specifically, comparing FIG. 4b, which represents a microscopy section of the different layers of a human skin explants after a 7-day exposure to an OVA patch in culture, with FIG. 4a, which represents a microscopy section of the different layers of a human skin explants after a 7-day exposure to a saline patch in culture. The images show that skin architecture is preserved regardless of the presence of ovalbumin antigen. However, OVA does induce alterations in skin structure, including thickening that is not shown in skin explants cultured with a saline patch.

FIG. 5 demonstrates a method that may be practiced on a skin explant to determine if a skin layer is thickening or thinning. Using this procedure, Table 4 shows significant epidermal thickening of a skin explant after seven days of culturing in the cell culture medium of the present invention with exposure to an OVA patch and compared to exposure to a saline patch in 3 out of 4 patients. For patient 2, the saline treated epidermis had a thickness of 72.795±2.741 μm and the OVA treated epidermis had a thickness of 87.129±3.557 μm, making the p value 0.005. For patient 4, the saline treated epidermis had a thickness of 61.651±2.393 μm and the OVA treated epidermis had a thickness of 61.899±6.136 μm, making the p value 0.824. For patient 8, the saline treated epidermis had a thickness of 62.646±1.673 μm and the OVA treated epidermis had a thickness of 70.067±1.026 μm, making the p value less than 0.001. For patient 9, the saline treated epidermis had a thickness of 49.073±1.829 μm and the OVA treated epidermis had a thickness of 67.414±2.883 μm, making the p value less than 0.001. These results support the success of cellular and molecular human skin explants cultured in the cell culture media and culture systems of the present invention in conjunction with an OVA patch.

TABLE 4

Epidermis thickness measurements for skin cell explants treated with OVA and saline.

| Patient | No. Analyzed Images | Saline (μm) | OVA (μm) | P |
|---|---|---|---|---|
| 2 | 10 | 72.795 ± 2.741 | 87.129 ± 3.557 | p = 0.005 |
| 4 | 10 | 61.651 ± 2.393 | 61.889 ± 6.136 | p = 0.824 |
| 8 | 10 | 62.646 ± 1.673 | 70.067 ± 1.026 | p < 0.001 |
| 9 | 10 | 49.073 ± 1.829 | 67.414 ± 2.883 | p < 0.001 |

FIG. 6 represents in situ human mast cell activation status for human skin explants grown in the cell culture medium of the present invention. FIG. 6 is a 40× digitized image of microcopy sections of human skin explants stained with methylene blue. The left image in FIG. 6 is of a human skin explant cultured for seven days with the cell culture medium of the present invention and a saline patch. As shown at the locations of the smaller or light gray circles, mast cells are still intact in various locations, and one activated mast cell is shown at the location of the larger dark gray circle. The right image in FIG. 6 is of a human skin explant cultured for seven days with the cell culture medium of the present invention and an OVA patch. As shown, there is an increase in the number of activated mast cells (indicative of degranulation) as for the skin explant treated with the OVA patch compared to the skin explant treated with the saline patch. FIG. 7 represents the quantification of in situ human mast cell activation status for the human skin explants grown in the cell culture medium of the present invention, where the data was obtained and quantified from images similar to those shown in FIG. 6, where the data was obtained from 4 female human subjects, and where 10 images were taken per subject. FIG. 7 illustrates that following a seven-day treatment with the cell culture medium of the present invention and an OVA patch or a saline patch, human skin explants cultured in the cell culture medium of the present invention with the OVA patch exhibited a statistically significant higher percentage of degranulated mast cells compared to the human skin explants treated with the cell culture medium of the present invention and a saline patch.

In summary, the results described above indicate that the application of OVA on the surface of ex vivo skin transplants can trigger enhanced skin mast cell activation and elevated levels of messenger RNA coding for chemokines compared to saline. Moreover, increased levels of skin Signal Transducer and Activator of Transcription (Stat)3 activation, a transcription factor that is activated in mast cells to enable chemokine and other inflammatory gene expression are shown in the OVA-treated skin punch biopsies, compared to the biopsied treated exposed to saline. Therefore, the use of the culture medium of the present invention can enable maintenance of human skin explants for up to or greater than 7 days in culture, allowing for cellular and molecular studies to be performed on human skin explants.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A mammalian skin explant culture system comprising:
   i. a culture medium, wherein the culture medium comprises Dulbecco's Modified Eagle's Medium, a serum free medium, subcutaneous adipocyte medium and from about 150 ng/mL to about 250 ng/mL recombinant human stem cell factor;
   ii. a vessel; and
   iii. an explant cover comprising an antigen, wherein the antigen is present in the explant cover from about 1 mg/mL to about 10 mg/mL.

2. The culture system of claim 1, wherein the vessel comprises a well plate.

3. The culture system of claim 1, further comprising a mammalian skin explant, wherein the mammalian skin explant is a human skin explant.

4. The culture system of claim 1, wherein the vessel comprises a humidified chamber that is configured to maintain a temperature and a $CO_2$ concentration.

5. The culture system of claim 4, wherein the temperature is approximately 25-48° C. and the $CO_2$ concentration is approximately 0-12% by volume.

6. The culture system of claim 5, wherein the temperature is approximately 28-44° C. and the $CO_2$ concentration is approximately 1-10% by volume.

7. The culture system of claim 5, wherein the temperature is approximately 30-39° C. and the $CO_2$ concentration is approximately 2-8% by volume.

8. The culture system of claim 5, wherein the temperature is approximately 37° C. and the $CO_2$ concentration is approximately 5% by volume.

9. The culture system of claim 3, wherein the mammalian skin explant is partially immersed in the culture medium within the vessel.

10. The culture system of claim 3, wherein the explant cover is in contact with a portion of the mammalian skin explant.

11. The culture system of claim 3, wherein the mammalian skin explant remains viable for at least three days.

12. A method of performing an in vitro study on a mammalian skin explant, wherein the in vitro study is performed after the mammalian skin explant remains viable in culture for at least three days using the culture system of claim 3.

13. The method of claim 12 wherein the in vitro study is an mRNA analysis.

14. The method of claim 12 wherein the in vitro study is a protein analysis.

15. The culture system of claim 1, wherein the antigen comprises ovalbumin antigen (OVA).

* * * * *